United States Patent
Zhou et al.

(10) Patent No.: US 7,048,693 B2
(45) Date of Patent: May 23, 2006

(54) SPECIMEN COLLECTION AND STORAGE AND TRANSPORT DEVICE AND METHOD

(75) Inventors: David F. Zhou, San Diego, CA (US); Nai Shu Wang, San Diego, CA (US); Claudia J. R. Shen, San Diego, CA (US); Angela J. Q. Shen, San Diego, CA (US)

(73) Assignee: Alfa Scientific Designs, Inc., Poway, CA (US)

( * ) Notice: Subject to any disclaimer, the term of this patent is extended or adjusted under 35 U.S.C. 154(b) by 0 days.

(21) Appl. No.: 10/766,135

(22) Filed: Jan. 27, 2004

(65) Prior Publication Data

US 2004/0184966 A1    Sep. 23, 2004

Related U.S. Application Data

(63) Continuation-in-part of application No. 10/407,496, filed on Apr. 3, 2003, now Pat. No. 6,921,370, which is a continuation-in-part of application No. 10/205,712, filed on Jul. 25, 2002, now Pat. No. 6,780,160.

(51) Int. Cl.
*A61B 10/00* (2006.01)

(52) U.S. Cl. ................................................. 600/562

(58) Field of Classification Search ............... 600/562; 604/317, 405; 73/864.91, 863.21; 422/102, 422/101, 61, 99; 435/307.1, 308.1; 206/569, 206/204, 570; 209/17, 173
See application file for complete search history.

(56) References Cited

U.S. PATENT DOCUMENTS 6,780,160 B1 *   8/2004   Zhou et al. ................. 600/562

FOREIGN PATENT DOCUMENTS

EP             0638803  A1 *   2/1995

* cited by examiner

*Primary Examiner*—Max F. Hindenburg
*Assistant Examiner*—Brian Szmal
(74) *Attorney, Agent, or Firm*—Charmasson, Buchaca & Leach, LLP

(57) ABSTRACT

A device for quantitively collecting, preserving and mailing a fresh and wet specimen of fecal or other biological matter for later analysis comprises a tubular vessel defining a chamber closed at one axial end by an openable, machine replaceable plug and restricted at the opposite end by a narrow aperture. A stopper for closing the open end of the vessel extends into a stick for dipping into and retaining some of the biological matter. The shank of the stick is dimensioned to seal the aperture once the stopper has been screwed upon the open end of the vessel. A cover caps the plug to provide additional sealing and protection of that end of the vessel during transportation. The vessel has a tapered shape to be carried closely packed with other similar vessels in a test carrier.

13 Claims, 5 Drawing Sheets

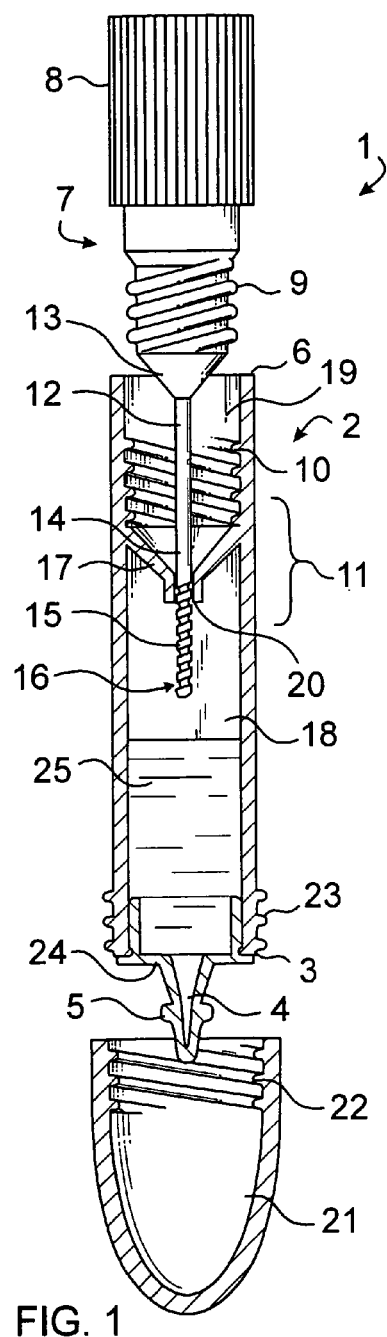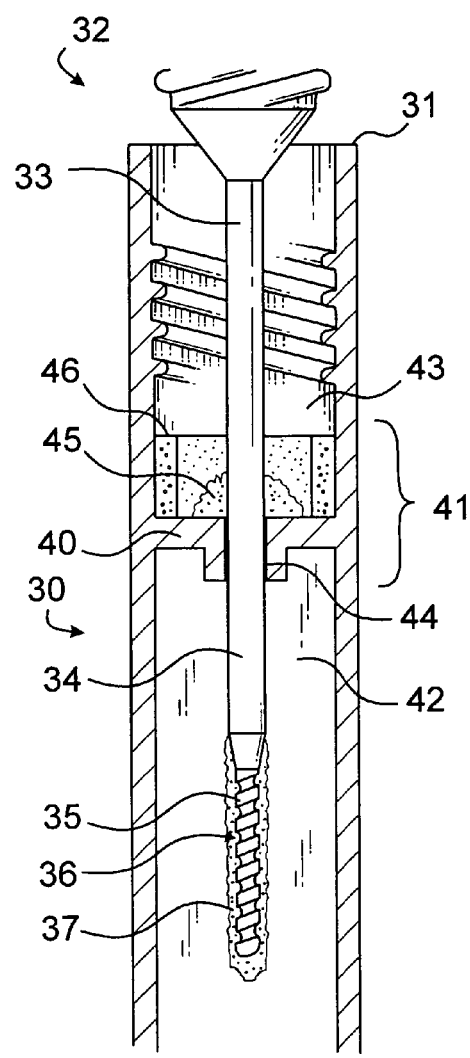
FIG. 1
FIG. 2

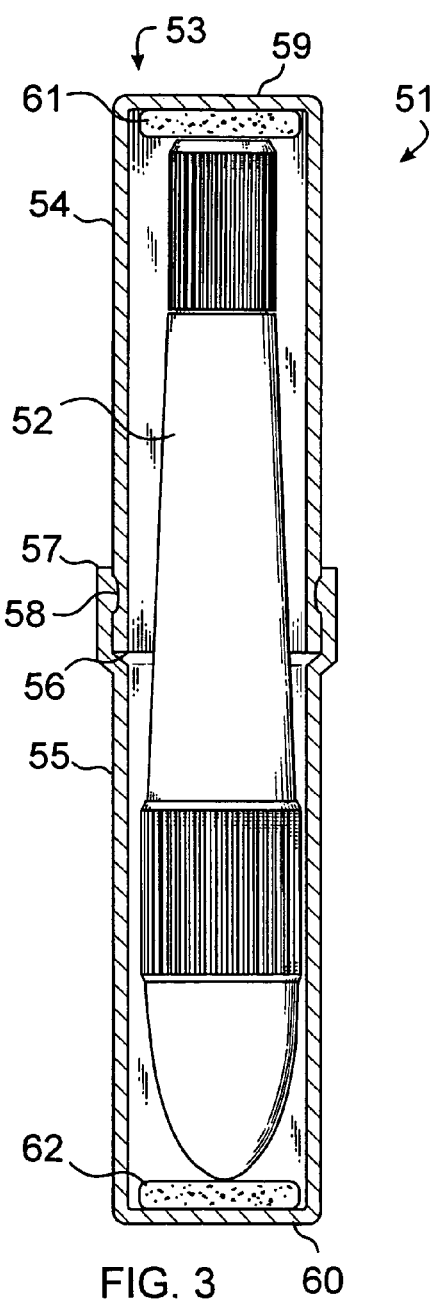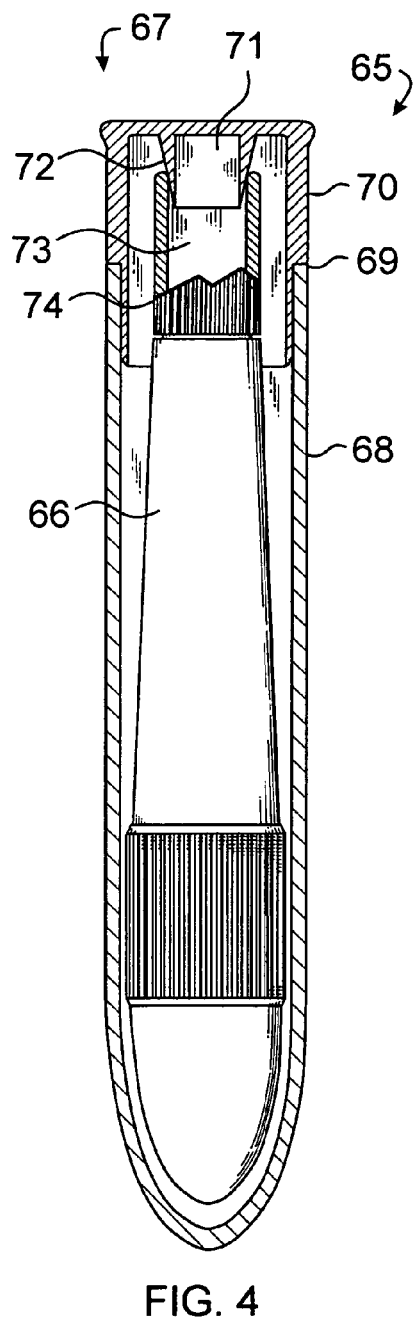

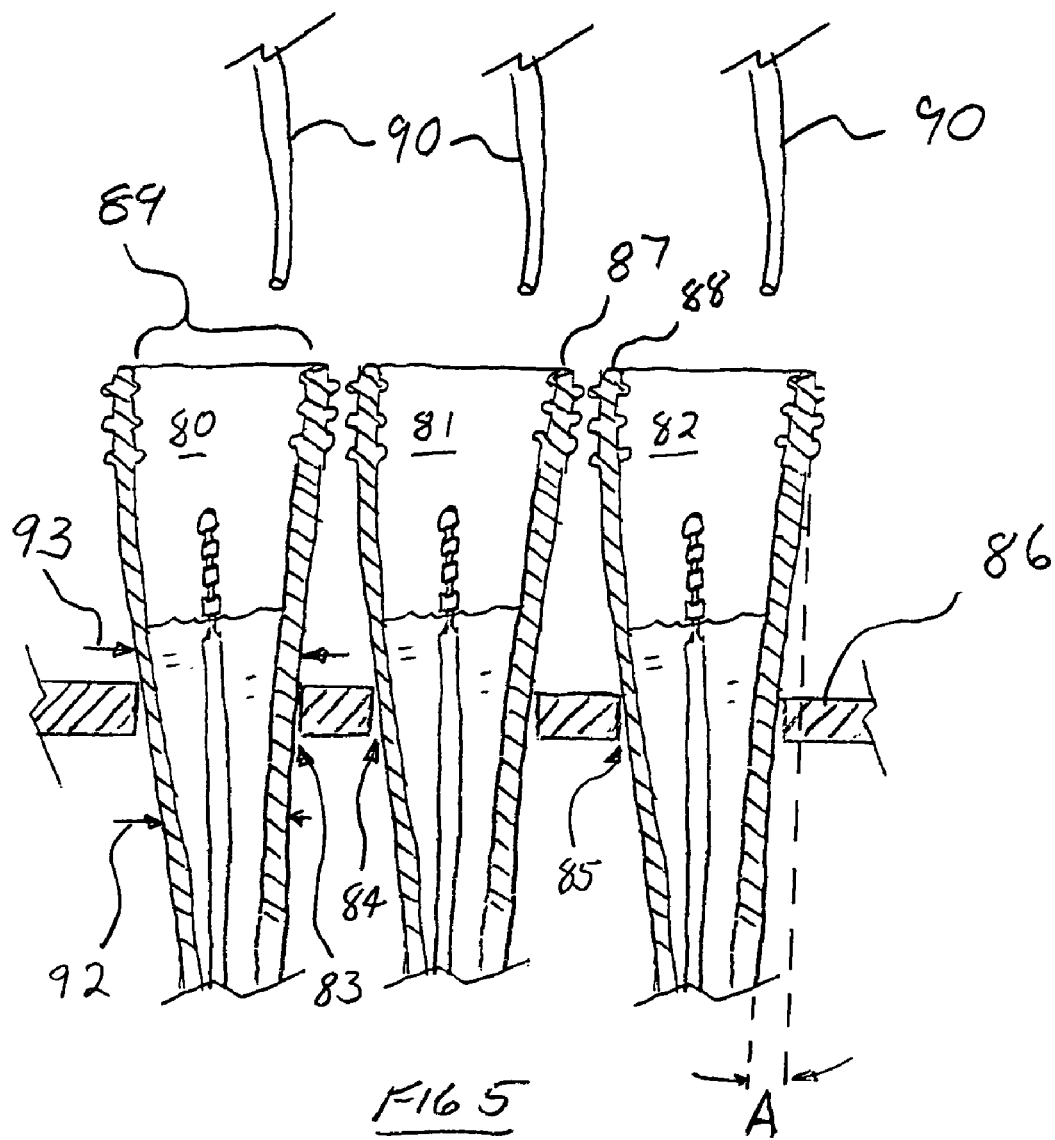

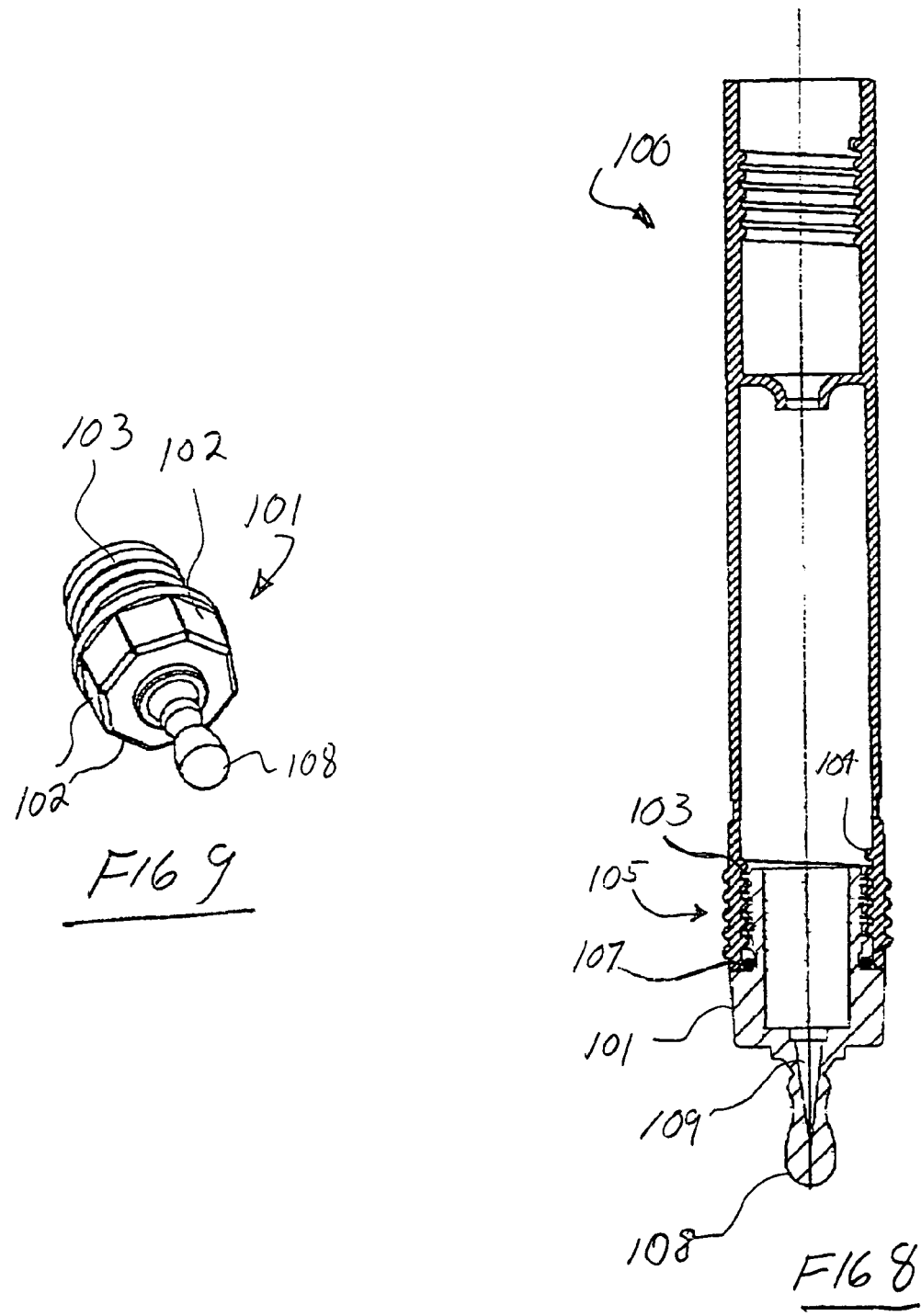

SPECIMEN COLLECTION AND STORAGE AND TRANSPORT DEVICE AND METHOD

PRIOR APPLICATION

This is a continuation-in-part of patent application Ser. No. 10/407,496 filed Apr. 3, 2003, now U.S. Pat. No. 6,921,370 which is a continuation-in-part of Ser. No. 10/205,712 filed Jul. 25, 2002, now U.S. Pat. No. 6,780,160.

FIELD OF THE INVENTION

This invention relates to methods and devices practiced and used in the collection, preservation, transportation and analysis of fluid, viscous or particulate solid or otherwise flowable or sequacious material samples of chemical, biological or environmental material including tissues, bodies, food, and soil, and more specifically to instruments used for specimens of fecal matter for screening the gastrointestinal tract for bleeding and colorectal cancer, or other similar biological materials.

BACKGROUND OF THE INVENTION

Several devices and methods have been used in the past to collect, preserve, transport and dispense chemical, environmental or biomedical specimens including fecal samples for later analysis by a laboratory or for clinical studies. The most common Guaiac Dye Test has been a dried smear paper pad, upon which, in the case of fecal samples, three consecutive specimens are smeared with dietary restrictions, covered then sent for analysis. One of the most common problems associated with this hundred years old device and method is dehydration. Even under rehydrating conditions, a fecal occult blood test of dry samples on paper pads will give a high rate of false positive or negative results. A false positive result may trigger a relatively expensive colonoscopic or barium enema examination that will probably or eventually eliminate the false diagnosis. In the case of a false negative result, an early stage colorectal cancer may be missed, and if then metastasis occurs, the cancer may become incurable.

Another fecal sample collection device of the prior art comprises a simple cylindrical tube with a cap having a breakable tip and a plastic stick connected to the inside of the screw cap. The tube contains a certain amount of extraction buffer. The stick is inserted into fresh feces several times then put back into the tube and the cap is tightly secured to seal the tube. The main advantage of this procedure is that the extraction buffer keeps the fresh specimen wet and a preserving reagent mixed therewith may slow down the degradation of the biological molecule or its markers. While this method constitutes a substantial improvement over the smear paper devices of the past, unintended breakdown of the tip on top of the cap has occurred during manipulation or mailing of the specimen resulting in leakage and possible contamination. Moreover, specimens have a tendency to include excessive amounts of fecal material for the fixed amount of preservative or reagent contained in the tube resulting in false positive analysis. Another improved device of the prior art is disclosed in U.S. Pat. No. 6,063,038 Diamond et al. In this case, a filtering membrane is provided between the body of the shipping vessel which holds the specimen and a preserving/reagent solution and the hollowed inside of the stick itself which can be accessed through a self-sealing membrane to extract a part of the liquid containing only the amount of specimen that passed through the filtering membrane. This improved device still suffers from a high risk of spillage of the preservative/reagent and a lack of quantitative mixing of the sample and preserving/reagent fluid.

Other devices provide for the dry storage of fecal material as disclosed in Kozak et al. U.S. Pat. No. 6,299,842 for purposes such as occult blood assays that detect labile exoantegens, but are not suited to carrying non-dry samples.

Due to the high cost of skilled labor used to manually manipulate and perform tests on the samples, devices which encourage greater automation and automation efficiency are generally preferred.

Because of the private and personal nature of fecal specimen collecting, collection is often performed by the relatively untrained donor. Further, because of the distasteful nature of feces, donors often have difficulty properly collecting or otherwise handling the fecal material. There is a need, therefore, for a device which reduces the handling of feces and the potential for close contact.

The instant invention results from some attempt to provide a practical solution to the problems and disadvantages of the aforesaid devices of the prior art.

SUMMARY OF THE INVENTION

The principal and secondary objects of this invention are to provide a convenient, safe and inexpensive to manufacture device and method for collection by a patient or unskilled person of fresh fecal or other biological, chemical or environmental specimens in a quantitatively metered manner and for the preservation and leakproof shipping of the specimen through the mail to a laboratory for further storage and analysis while avoiding degradation of the specimen through unwanted dehydration or the imbalanced combination of specimen and preserving agents, and optionally providing for preservation of an amount of dry material.

These and other valuable objects are achieved by providing a simple tubular vessel closed at one end by a breakable hollow nib or other releasable sealing device, that is engaged at the opposite end by a cap or stopper from which a stick axially projects into the vessel. At the distal end of the tip, a sample-holding portion has at least one radial or axial cavity and preferably indentations in the form of a spiral or helicoidal groove. As the stopper and stick are progressively inserted into the vessel by a screwing movement, the sample-holding portion passes through an aperture defining a narrow channel in the center of a septum in the median section of the vessel. The cross-section of the non-grooved part of the sample-holding portion and/or the shank portion adjacent to the sample-holding portion closely match the cross-sectional profile of the aperture so that any excess specimen matter which is not contained within the profile, is conveniently wiped out and prevented from passing into the most distal chamber of the vessel that contains a preserving fluid. Optionally, the excess specimen is usefully stored in the proximal chamber in the presence of a desiccant or drying material. The shank of the stick right behind the sample-holding portion seals the specimen-holding chamber so that the amount of specimen and preserving fluid are quantitatively balanced and remain so until part or all of the fluid is extracted for analysis after breaking of the sealing nib. A cover, shaped and dimensioned to safely cap the breakable nib can be tightly screwed upon the closed end of the vessel to protect the nib during manipulation and shipping of the device. The wet specimen-holding chamber is thus doubly sealed at opposite ends to ensure against leakage both before and after specimen collection. A padded or spring suspension shipping container made from inexpensive disposable plastic provides a third seal and enhanced protection. A disposable, telescopingly extendible handle is conveniently provided within the shipping container. The handle is shaped at one end to temporarily secure to the stopper opposite the stick allowing the collector to stab at feces in a toilet without contacting the toilet water by hand. The outer surface of the vessel can be shaped to have a gentle taper which allows more close packing of an array of adjacent vessels in a test carrier. The plug can be further adapted to allow it to be releasably mountable to the vessel using common automated machinery.

BRIEF DESCRIPTION OF THE DRAWING

FIG. 1 is a cross-sectional side view of a biological specimen-collecting device according to the invention;

FIG. 2 is a partial cross-sectional side view of the septum portion of an alternate embodiment of a specimen-collecting device according to the invention;

FIG. 3 is a diagrammatic cross-sectional side view of the device of FIG. 1 carried within a shock-resistant transport capsule;

FIG. 4 is a diagrammatic cross-sectional side view of the device of FIG. 1 carried within an alternate embodiment of the shock-resistant transport capsule;

FIG. 5 is a diagrammatic cross-sectional side view of a plurality of devices according to FIG. 4 loaded into an automated testing carriage;

FIG. 8 is a diagrammatic cross-sectional side view of an alternate embodiment of a specimen collecting device according to the invention; and FIG. 9 is a diagrammatic perspective view of the end section plug of the device of FIG. 8.

Figure 6:
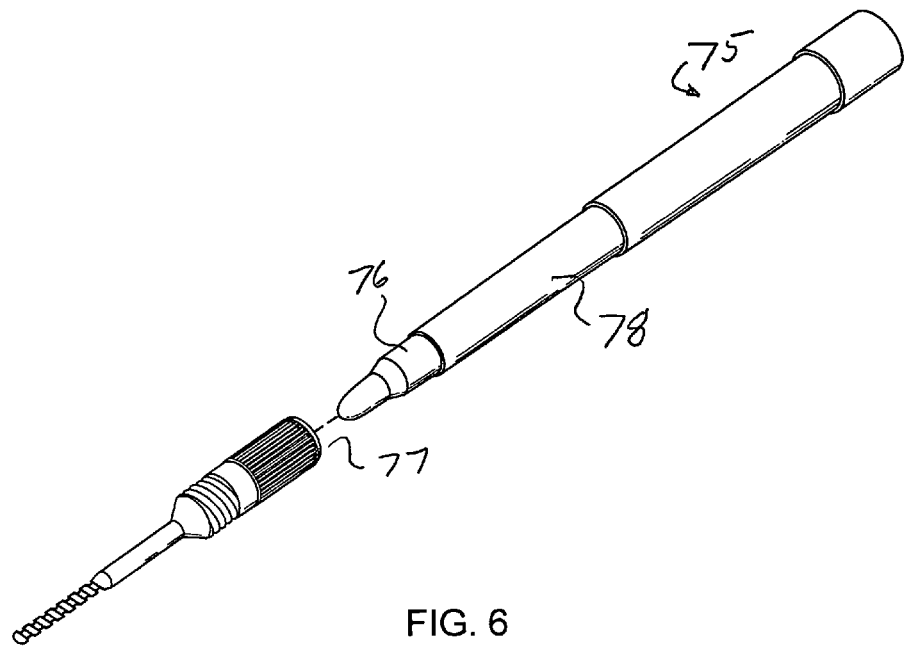
FIG. 6 is a diagrammatic perspective view of an extended handle for mounting the stopper for toilet sampling.

DESCRIPTION OF THE PREFERRED
EMBODIMENT OF THE INVENTION

Referring now to the drawing, there is shown a first embodiment of a device 1 specially adapted to collect a specimen of fecal or other chemical or biological matter, store and preserve it while it is mailed to a laboratory for analysis. The device comprises a tubular, preferably cylindrical, vessel 2 having a first end 3 closed and defining an access port 4 which is releasably sealed by a hollow nib 5 that can be easily broken to open the access port and allow convenient dispensing. The opposite, normally open, end 6 of the vessel is engaged by a stopper 7 comprising a knob 8 and a threaded plunger 9. Screw threads 10 matingly cooperating with the threaded plunger are provided along the inside wall of the vessel from the second end 6 down to a median portion 11 of the vessel. A stick 12 projects axially from the stopper, more specifically, from the conical distal end 13 of the plunger into the vessel. The stick comprises a shank 14 and a sample-holding distal portion 15. The sample-holding portion consists an oblong cylindrical member into which indentations 16 in the form of an helicoidal groove have been cut. The radius of the distal portion is substantially the same as the radius of the cylindrical shank 14.

A conical transversal septum 17 in the median portion 11 of the vessel divides the vessel into a first chamber 18 sealed by the closed end 3 and a second chamber 19 accessible through the second end 6. An aperture or passageway 20 in the middle of the septum is axially lined up with the stick 12 and has a cross-sectional geometry substantially symmetrical with that of the stick, that is a radius substantially equal to the radius of the shank 14 and sample-holding portion 15. The cooperatively conically shaped distal end 13 of the plunger and septum 17 allow for enahnced resiliency, thereby providing a positive seal over a larger range of plunger positions.

When the knob 8 of the stopper is turned clockwise, the sample-holding portion 15 of the stick progressively translates from the second chamber 19 into the first chamber 18 through the passageway constituted by the aperture 20 until such time as a distal part of the shank 14 engages and seals the aperture.

A cover 21 shaped and dimensioned to cap the closed first end 3 and end-breakable nib 5 has a threaded inner wall section 22 that cooperates with a correspondingly threaded area 23 on the outer wall of the vessel to secure the cover and thus, protect the breakable nib 5.

The end section 24 that mounts the breakable nib 5 at the first end 3 of the vessel is not molded integrally with the wall of the vessel, but constitutes a separate plug which is installed only after the first chamber 18 has been filled with the preserving fluid 25. The end section 24 is preferably bonded to the vessel to seal against fluid leaks. Such bonding can be permanent through use of an adhesive for example, or semi-permanent by dimensioning the plug to create a pressure seal for example. Alternately, the bond can be machine removable as described in a later embodiment. It should be noted that this bonding of the end section and the cover 21 that further occludes both the access port 4 controlled by the breakable nib and the one sealed by the end section plug 24, combined with the double seal provided by the shank 14 of the stick closing the aperture 20 and the stopper 7 closing the second end 6 of the vessel assures against any leakage of the preserving fluid during shipment, before and after collection of the specimen.

The device may be used as follows. At the factory, with plunger 9 fully or partially screwed into the second end of the vessel and the aperture 20 sealed, a measured volume of preserving liquid 25 is introduced into the first chamber through the first end 3 which is then sealed by the installation and bonding of the end section 24. The volume is measured to provide the desired concentration of specimen that will eventually be found in suspension in the liquid. The device is marked about the first end 3, such as on the cover 21, with a legend such as "For Laboratory Use" or "Lab End". The knob 8 or upper area of the vessel is marked with another legend such as "Open Here" or "Patient End". The device is then packaged and distributed for use.

The collection of the specimen by the patient or an assisting individual goes as follows. Holding the stopper 7 by the knob and after unscrewing it and separating it from the vessel, the user plunges the sample-holding portion 15 of the stick into a volume of matter to be analyzed. The stick is then inserted back into the vessel and the stopper is screwed down until the sample-holding portion passes completely through the aperture 20 of the septum. During this procedure, the walls of the aperture coming into intimate contact with the non-threaded part of the sample-holding portion and shank, wipe out any excess material which is not held within the helicoidal groove, preventing that excess material from reaching the first chamber. Accordingly, only a quantitively metered amount of specimen matter is allowed into the first chamber. The first chamber contains the metered volume of preserving fluid 25, preferably a liquid which will remain in contact with the specimen matter throughout storage and transportation of the vessel until part or all of it is drained for analysis by breaking the nib 5.

It should be noted that the preserving liquid in the first chamber could be safely secured initially by a breakable barrier across the aperture 20 of the septum or by a resiliently self-sealing aperture. In which case, at the factory, the stopper would be only partially engaged into the vessel, keeping the sample-holding portion into the second chamber. Only after collection of the specimen would the stopper be completely screwed into the vessel and the sample-holding portion forced through the septum. Instead of the end section 24, the first end of the vessel could be closed by a diaphragm through which a self-sealing access port can be practiced by means of a syringe or any other equivalent releasable sealing structure.

Referring now to FIG. 2, there is shown the median portion of an alternate embodiment of the device for collecting, storing, preserving, transporting and analyzing chemical or biological samples such as fecal specimens wherein a vessel 30 having an end 31 engaged by a stopper 32 having an axially projecting stick 33 which comprises a shank 34 and an oblong cylindrical sample-holding distal portion 35 having indentations 36 in the form of a helicoidal groove. The radius of the distal portion is substantially smaller than the radius of the cylindrical shank thereby allowing a greater amount of sample material 37 to be carried thereon.

A cylindrical transversal septum 40 in the median portion 41 of the vessel divides the vessel into a first chamber 42 and a second chamber 43. An aperture or passageway 44 in the middle of the septum is sized to closely bear against the shank 34 of the stick 33 so that the aperture is effectively sealed by the stick.

Translation of the stick 33 from the second chamber 43 into the first chamber 42 through the passageway causes accumulation of an amount of excess sample 45 on the surface of the septum 40 facing the second chamber 43. A hollow cylindrical disk of dessicant 46 such as silica gel or clay is located inside the second chamber proximate to the septum 40.

Referring now to FIG. 3, there is shown an alternate embodiment of a device 51 for collecting, storing and protectively transporting fecal or other similar chemical, biological or environmental material. The device formed similarly to the previous embodiment has a generally cylindrical vessel 52 having a gently tapering diameter. The entire vessel is loadable into a sealable shipping capsule 53 which comprises a pair of open-ended cups 54, 55 matable at the open ends 56, 57 along an annular snap connector 58. Each cup has a closed end 59, 60 having cushion pad 61, 62 formed onto the inner surface. The capsule is preferably made from an inexpensive, durable, fluid-resistant material such as polyethylene plastic.

Referring now to FIG. 4, there is shown an alternate embodiment of a device 65 for collecting, storing and protectively transporting fecal or other similar chemical biological matter. The device formed similarly to the previous embodiment has a generally cylindrical vessel 66 having a gently tapering diameter. The entire vessel is loadable into a sealable shipping capsule 67 which comprises an oblong cup 68 having an open end 69 and an end cap 70 for closing the capsule. The end cup is preferably formed to have an axially located spring pedestal 71 having a frustoconical outer surface 72 sized to engage and bear against a cylindrical pocket 73 axially formed into an end of the knob 74 of the stopper of the vessel 66. The end cap is formed from a material which allows a slight flexibility in the pedestal thereby providing a shock-resistant, springing support for the vessel. The capsule is preferably made from an inexpensive, durable, fluid-resistant material such as polyethylene plastic.

Referring now to FIG. 5, there is shown a number of generally cylindrical vessels 80, 81, 82 having a gently tapering diameter as in the device of FIG. 4. The overall taper has been greatly exaggerated in this figure to show that each vessel can be readily inserted into one of an array of adjacent holes 83, 84, 85 in a testing carriage 86. The taper allows each vessel to be inserted narrow diameter end first into a hole where in sinks through the hole until the increasing diameter reaches the inside diameter of the hole. The structure of the vessel can therefore be said to have an axially medial surface portion 92 having a narrower diameter or axial cross-section than an adjacent axially medial surface portion 93. In this way, the vessel is securely held in place within the carriage. Adjacent vessels are similarly held. The tapering allows a close bunching together of adjacent vessels, even allowing contact between adjacent vessels at the broad diameter end 87, 88, thereby allowing the carriage to carry an increased number of vessels. This structure also provides a wider top opening 89 allowing for greater error in the location of each of the flexible testing probes 90 which access the fluid within the vessel in an automated testing fashion. The angle A formed between the vertical and the tapered surface of the vessel is selected to provide close packing while accommodating existing carriers and providing adequate vessel volume. In most common applications for a linear taper, the angle A is preferably between about 0.25 and 5.0 degrees. Although the present embodiment discloses a linear taper providing a generally frusto-conical shape to the vessel, those skilled in the art will readily appreciate non-linear tapers. Referring now to FIG. 6, there is shown telescopingly extendible handle 75 having a tapered tip portion 76 sized and shaped to frictionally and releasably engage a cylindrical pocket 77 axially formed into the end of the knob portion of a stopper. The handle further comprises a medial telescoping member 78 coaxially formed about the end prong member and coaxially and slidingly mounted within a proximal handle portion member. The handle allows the user to conveniently collect a fecal sample from a toilet without contacting the toilet water.

Figure 7:
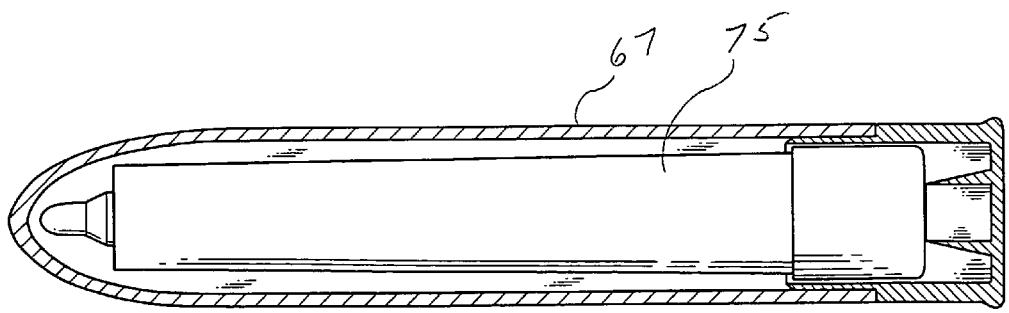
FIG. 7 is a cross-sectional side view of the transport container of FIG. 4 carrying the collapsed handle of FIG. 6.

Referring now to FIG. 7, there is shown the handle 75 in a collapsed configuration having overall dimensions which allow it to be stored within the capsule 67 of FIG. 4. In this way, the vessel capsule and handle can be efficiently packaged and provided to the user.

Referring now to FIGS. 8 and 9, there is shown an alternate embodiment of the device for collecting, storing and protectively transporting fecal or other similar chemical or biological matter. In this embodiment, the device has a generally cylindrical vessel 100 similar to the previous embodiments, however, in this embodiment, the end portion plug 101 is adapted to be readily secured and removed in an automated fashion by having a machine graspable radial outer surface having a plurality of facets 102 similar to the radial outer surface of a standard nut fastener. The plug is further formed to have an outer male threaded portion 103 on a first end and a breakable nib 108 on an opposite end which opens an access port 109. The threaded portion 103 of the plug releasably engages an inner female threaded portion 104 in the end portion 105 of the vessel 100. In this way, automated machinery can remove and replace the plug. To further encourage automated engagement of the facets, the surface of each facet may be angled inwardly toward the nib end of the plug. A resilient circumferential O-ring 107 provides for greater sealing against fluid leaks.

While the preferred embodiments of the invention have been described, modifications can be made and other embodiments may be devised without departing from the spirit of the invention and the scope of the appended claims.

What is claimed is:

1. A device, for quantitatively collecting, preserving and transporting a specimen of material for later analysis, which comprises:
    a vessel having a first closed end defining at least one sealed access port, a second open end opposite said first end;
    a stopper shaped and dimensioned to close said open end;
    a cover releasably occluding said sealed access port; and,
    wherein said sealed access port is releasably sealed by a removably and replaceable plug.

2. The device of claim 1, wherein said plug is threaded to releasably engage said first closed end having cooperative threads.

3. The device of claim 1, wherein said plug comprises a machine graspable outer surface.

4. The device of claim 3, wherein said machine graspable outer surface comprises a faceted surface.

5. The device of claim 1, wherein said vessel has a tapered outer surface.

6. The device of claim 5, wherein said tapered outer surface is oriented to create a first axially medial surface portion having a narrower axial cross-section than a second axially medial surface portion.

7. The device of claim 6, wherein said second axially medial surface portion is located closer to said first closed end than said first axially medial surface portion.

8. The device of claim 5, wherein said tapered outer surface has a substantially frustro-conical shape.

9. The device of claim 1, wherein said sealed access port comprises an end-breakable hollow nib.

10. The device of claim 9, which further comprises a shaped and dimensioned to cap said closed end and nib.

11. The device of claim 1, wherein the open end of said vessel and said cover have cooperative screw threads.

12. The device of claim 1 which further comprises an outer transport capsule sized and shaped to fully enclose said vessel, stopper, and cover.

13. The device of claim 1, which further comprises an amount of desiccant located in said vessel.

* * * * *